United States Patent [19]

Kiefer

[11] Patent Number: 4,482,492

[45] Date of Patent: Nov. 13, 1984

[54] PREPARATION OF VITAMINS $K_3$ AND $K_4$ AND DERIVATIVES

[75] Inventor: Hans Kiefer, Wachenheim, Fed. Rep. of Germany

[73] Assignee: BASF Aktiengesellschaft, Fed. Rep. of Germany

[21] Appl. No.: 434,832

[22] Filed: Oct. 18, 1982

[30] Foreign Application Priority Data

Oct. 19, 1981 [DE] Fed. Rep. of Germany ....... 3141443

[51] Int. Cl.$^3$ .............................................. C07C 50/14
[52] U.S. Cl. ............................ 260/396 K; 260/396 R
[58] Field of Search ........................ 260/396 R, 396 K

[56] References Cited

U.S. PATENT DOCUMENTS

| | | | |
|---|---|---|---|
| 2,348,976 | 5/1944 | Hyman | 260/396 |
| 2,352,189 | 6/1944 | Fernholz | 260/396 |
| 2,379,460 | 7/1945 | Scott | 260/396 |
| 2,585,229 | 2/1952 | Coover, Jr. et al. | 260/396 |

OTHER PUBLICATIONS

Vitamine, VEB Gustav Fischer Verlag, Jena, 1965, pp. 1050–1056.
Houben-Weyl, vol. VII/3a, (1977), pp. 80–85.
Hill and Carlson, *Journal of Organic Chemistry*, vol. 30, pp. 2414–2417, "A Direct Method for the Construction of Benzene Rings", 1965.

*Primary Examiner*—Glennon H. Hollrah
*Assistant Examiner*—Raymond Covington
*Attorney, Agent, or Firm*—Keil & Weinkauf

[57] ABSTRACT

Vitamin $K_3$ (I; 2-methylnaphtho-1,4-quinone), vitamin $K_4$ (IIa; 2-methyl-1,4-dihydroxynaphthalene) and vitamin $K_4$ diacetate (IIb) are prepared by reacting 1-acetoxy-buta-1,3-diene (IV) with methylbenzoquinone (V) to give the novel compounds IIIa and IIIb

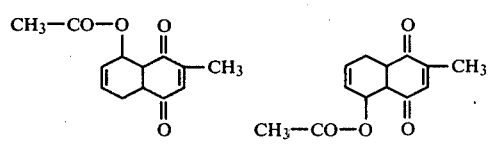

and, for the preparation of IIa, deacetylating these compounds, or, for the preparation of IIb, deacetylating these compounds and at the same time reacting them with acetic anhydride, or, for the preparation of I, deacetylating these compounds and at the same time oxidizing them.

6 Claims, No Drawings

PREPARATION OF VITAMINS K₃ AND K₄ AND DERIVATIVES

The present invention relates to a novel process for the preparation of vitamins $K_3$ and $K_4$ and of derivatives thereof. These compounds have the following formulae I to IIIb:

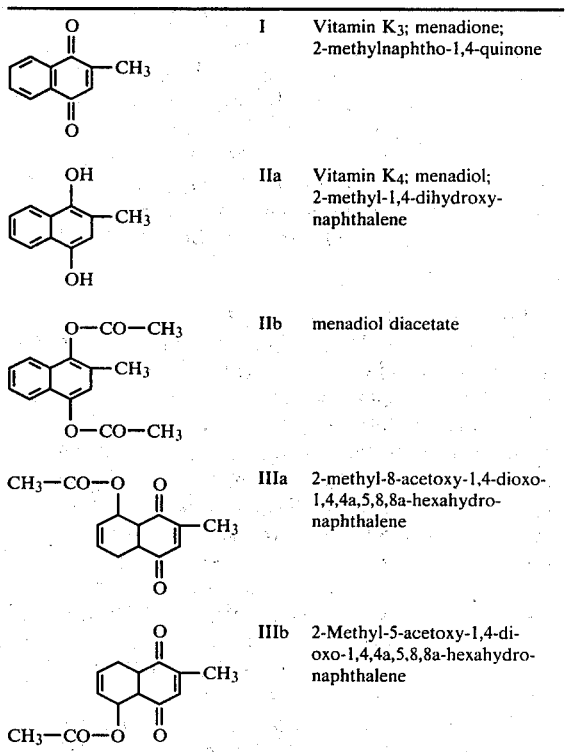

The invention also relates to the novel intermediates IIIa and IIIb.

The antihemorrhagic vitamins of the K group (coagulation vitamins), and amongst these vitamins $K_3$ (I) and $K_4$ (IIa) and the diacetate of vitamin $K_4$ (IIb) are known to be used as hemostatic medicaments, and moreover are of great importance in animal nutrition.

Of the various methods for the preparation of I (cf. Vitamine, VEB Gustav Fischer Verlag, Jena, 1965, page 1050 et seq.), only oxidation of 2-methylnaphthalene with chromic and sulfuric acids has hitherto been adopted, although the yield of this process is only from 20 to 40% and the use of chromic and sulfuric acids causes substantial technological difficulties. Since IIa has hitherto been prepared by reduction of I and IIb has hitherto been prepared by acetylation of IIa, IIa and IIb have also been accessible only by the unsatisfactory route of oxidation of 2-methylnaphthalene.

Various naphthoquinone syntheses by Diels-Alder reaction of a 1,4-diene with benzoquinone or a benzoquinone derivative, such as methylbenzoquinone, are known from Houben-Weyl, Volume VII/3a, 1977, page 80 et seq. Specifically, these syntheses comprise the following reactions:

The reaction of butadiene with benzoquinone and subsequent oxidation with $CrO_3$; this process is tedious and cumbersome, and moreover requires the use of $CrO_3$, which presents technological disadvantages;

The reaction of 1,4-diacetoxybutadiene with benzoquinone; this reaction requires heating of the reactants for 4 days, and thus is also unsuitable for technical purposes;

The reaction of cyclohexa-1,3-diene and 2-methylbenzoquinone, isomerization of the Diels-Alder adduct with $HBr/H_2O$ to give the corresponding hydroquinone derivative, oxidation of the latter compound with $FeCl_3$ and elimination of ethylene by the action of heat to give I; this route is also obviously cumbersome and therefore unsuitable for a technical synthesis;

Reaction of crotonaldehyde with ethoxy-Mg-Br to give butadiene-1-oxy-Mg-Br, adduct formation between the product and methylbenzoquinone, elimination of MgBrOH and oxidation of the hydroquinone to give I; apart from the fact that the use of organomagnesium compounds is also cumbersome and uneconomical, the yields in this reaction are unsatisfactory.

It is an object of the present invention to produce the important compounds I, IIa and IIb in a simpler and more economic manner than hitherto. I have found that this object is achieved, and that vitamin $K_3$ (I), vitamin $K_4$ (IIa) and the diacetate of vitamin $K_4$ (IIb)

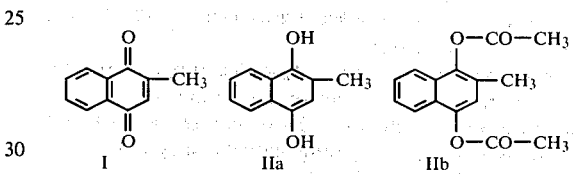

and the intermediates IIIa and IIIb of these compounds

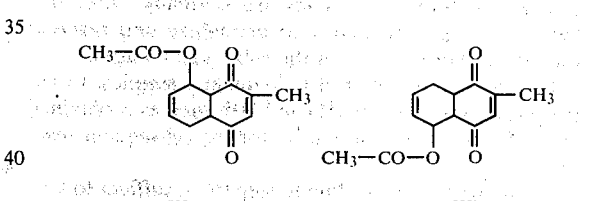

are obtained in remarkable reaction sequences wherein
(a) 1-acetoxybuta-1,3-diene (IV) and 2-methylbenzo-1,4-quinone (V) are reacted with one another at from 20° to 100° C. to give a mixture of IIIa and IIIb and these compounds are isolated in a conventional manner or, as a mixture or after being isolated,
(b) for the preparation of IIa, are heated to not more than 200° C. and/or treated with a non-oxidizing acid,
(c) for the preparation of IIb, are heated, together with acetic anhydride, to from 50° to 150° C., or
(d) for the preparation of I, are heated, together with an oxidizing agent, to from 20° to 100° C.

All reaction steps of this process proceed unexpectedly smoothly, and the yield of the process is not less than 80%, based on the methylbenzoquinone used. Compared to the prior art described, the easy deacetylation of the intermediates IIIa and IIIb is particularly surprising.

The starting compound IV, 1-acetoxy-buta-1,3-diene, is known and can easily be obtained in good yields by reacting crotonaldehyde with acetic anhydride (cf., eg., J. Org. Chem., 21 (1956), 330). It has been found that the trans-form of IV reacts particularly smoothly with V to give IIIa and IIIb.

The starting compound V, methylbenzo-1,4-quinone, which is also known, can advantageously be prepared by oxidizing o-toluidine with manganese dioxide.

Reaction step (a), a Diels-Alder adduct formation of IV with V, is effected without difficulties, preferably at from 40° to 80° C. If the temperature rises above 80° C., partial deacetylation to give IIa takes place, which, from an economic point of view, is disadvantageous inasmuch as IIa is oxidized to I by using up V, ie. V functions as a relatively expensive oxidizing agent, where a cheaper oxidizing agent fulfils the same purpose.

Reaction (a) is advantageously carried out in the presence of a solvent, such as any inert organic liquid in which both IV and V are soluble, eg. dimethylformamide, toluene, xylene, N-methylpyrrolidone, acetonitrile and ethyl methyl ketone. $C_5$-$C_8$-Alkanes and cycloalkanes, eg. cyclopentane and cyclohexane, are particularly suitable since the compounds IIIa and IIIb formed are insoluble in these solvents and separate out as oils and are thus removed from any undesirable side reactions.

IV is preferably used in a 10-20% molar excess over V, and the amount of solvent is as a rule from 2 to 10 kg per kg of feed mixture.

Since reaction (a) proceeds under atmospheric pressure, there is generally no reason to apply reduced or superatmospheric pressure. However, the latter may be advantageous if a low-boiling solvent, such as butane or methylene chloride, is used.

A mixture of about 30% of IIIa and 70% of IIIb is usually obtained, and previous observations have shown that both compounds are sterically pure, IIIb having a greater tendency to crystallize and reacting somewhat more readily in the subsequent stages.

In industry, however, it is frequently simplest to use the reaction mixture of IIIa and IIIb such as is obtained in the Diels-Alder reaction (a) for the subsequent reactions.

To prepare IIa according to step (b), it suffices to heat the compound IIIa or IIIb or a mixture thereof for from 1 to 5 hours at 100°-200° C. This reaction can be accelerated by the presence of an acid, for example acetic acid, in which case the temperature can be lowered accordingly. If a strong non-oxidizing acid, such as hydrochloric acid, aqueous sulfuric acid, phosphoric acid or an acidic ion exchanger is used, heating can be dispensed with entirely, ie. in that case the reaction is preferably carried out at room temperature or only slightly elevated temperature (up to about 60° C.). The choice between these various possibilities, namely heating without an acid, moderate heating in the presence of an acid, or treatment with an acid without heating, depends on the particular economic and technical considerations. The amount of acids can be varied over a wide range, namely from about 0.01 to 10 moles per mole of IIIa or IIIb.

As regards pressure, the same considerations apply as for step (a), ie. as a rule the process is carried out under atmospheric pressure.

If compounds IIb are to be prepared according to step (c), the same conditions apply as for step (b) except that the reaction is carried out in the presence of from 2 to 6 moles of acetic anhydride per mole of the starting compound IIIa and/or IIIb. This reaction can be accelerated by catalytic amounts of acetyl chloride. In order to avoid a reduction of yield by undesired oxidations to the quinone, it can be advisable to effect the reaction in the presence of a small amount of zinc dust.

A similar situation applies to step (d), namely the preparation of I from IIIa and/or IIIb. In that case the reaction is advantageously carried out in the presence of from 2 to 8 moles of an oxidizing agent per mole of IIIa or IIIb. Examples of suitable oxidizing agents are hydrogen peroxide and especially sodium nitrite and nitric acid.

The use of solvents in process steps (b) to (d) is not essential but can be advantageous to ensure a more uniform reaction and facilitate working up of the reaction mixtures. Examples of suitable solvents are benzene, toluene, xylene and acetic acid.

Working up the reaction mixtures to give the products presents no fundamental problems and can therefore be effected in a conventional manner. Similar remarks apply to the purification of the compounds.

EXAMPLE 1

Preparation of compounds IIIa and IIIb 135 g (1.2 moles) of acetoxybuta-1,3-diene were added, over one hour, to a mixture of 122 g (1 mole) of methyl-p-benzoquinone and 400 ml of n-heptane, after which the reaction mixture was kept at 60° C. for 4 hours. When the mixture cooled to room temperature, an oily phase separated out, and this was separated off and washed with twice 100 ml of n-heptane. Thereafter the remaining solvent and excess acetoxybutadiene were removed under reduced pressure at 60° C. The oil which remained and which, according to NMR analysis, contained the two isomers IIIa and IIIb in the ratio of 30:70, solidified after some time to give colorless crystals of melting point 73°-90° C.; yield 96%, based on methylbenzoquinone employed.

Recrystallizing the mixture from 800 ml of methanol gave the preferentially crystallizing isomer IIIb in a pure form; melting point 99° C., yield about 60% based on methylbenzoquinone employed.

EXAMPLE 2

Preparation of compound IIa 122 g (1 mole) of methylbenzoquinone and 135 g (1.2 moles) of acetoxybutadiene were first reacted, similarly to Example 1 but using 300 ml of o-xylene as the solvent in place of heptane, to give a mixture of the isomers IIIa and IIIb.

The xylene solution thus obtained was then freed from atmospheric oxygen by passage of nitrogen, and was thereafter refluxed (at 144° C.) for 4 hours.

The reaction mixture was then cooled, whereupon IIa separated out as a colorless precipitate; melting point 177°-178° C.; yield 81% based on methylbenzoquinone employed.

EXAMPLE 3

Preparation of compound IIa 23.4 g (0.1 mole) of IIIb were introduced, with stirring, into 100 ml of 20% strength by weight hydrochloric acid (about 0.6 mole of HCl). The mixture was heated to 30°-40° C., whereupon compound IIIb dissolved. Immediately thereafter, colorless crystals of IIa separated out.

100 ml of water were added to ensure that IIa had separated out completely. The yield of IIa was 95%, based on IIIb employed.

The use of 100 ml of 50% strength by weight phosphoric acid in place of hydrochloric acid proved equally successful.

EXAMPLE 4

Preparation of I 23.4 g (0.1 mole) of the mixture of isomers IIIa and IIIb, prepared as described in Example 1, were added, over 20 minutes, to 250 ml of 30% strength by weight aqueous nitric acid (about 0.7 mole of $HNO_3$) at 50°–60° C., with vigorous stirring. The mixture was then stirred for a further hour at 50°–60° C. and thereafter cooled, whereupon I was obtained in the form of yellow crystals. The product was filtered off, washed with water and dried. Impurities were no longer detectable by gas-chromatographic analysis; melting point 105° C.; yield 86%.

EXAMPLE 5

Preparation of IIb

An isomer mixture of IIIa and IIIb was first prepared, similarly to Example 1 but using 400 ml of pure acetic acid as the solvent, from 122 g (1 mole) of methylbenzoquinone and 123 g (1.1 moles) of acetoxybutadiene.

The mixture thus obtained was subsequently refluxed for 4 hours with 408 g (4 moles) of acetic anhydride and 5 g of acetyl chloride, under nitrogen. It was then heated with 2 g of zinc powder for 30 minutes, filtered and worked up by distillation. The main fraction obtained (at 0.01 mbar/160° C.) was a colorless oil which solidified to crystals of melting point 109° C.

Recrystallization of this material gave pure IIb in a yield of 85%; melting point 115° C.

EXAMPLE 6

Preparation of I

An acetic acid solution of IIIa and IIIb, prepared in accordance with the first paragraph of Example 5, was boiled for 5 hours; a solution of 600 ml of water and 376 g (about 5.5 moles) of sodium nitrite was added at 50°–60° C. and the mixture was kept at this temperature for one hour, during which I was obtained in the form of a yellow crystalline precipitate. Conventional working up gave pure I in 87% yield, based on methylbenzoquinone employed.

I claim:

1. 2-Methyl-8-acetoxy-1,4-dioxo-1,4,4a,5,8,8a-hexahydronaphthalene (IIIa).

2. 2-Methyl-5-acetoxy-1,4-dioxo-1,4,4a,5,8,8a-hexahydronaphthalene (IIIb).

3. A process for the preparation of the compounds

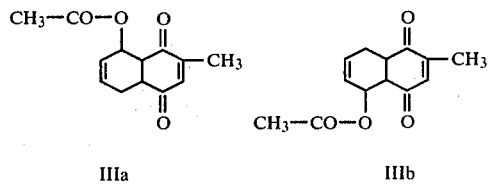

which comprises: reacting 1-acetoxybuta-1,3-diene (IV) and 2-methylbenzo-1,4-quinone (V) at from 20° to 100° C. to give a mixture of IIIa and IIIb.

4. A process for producing vitamin $K_4$ of the formula

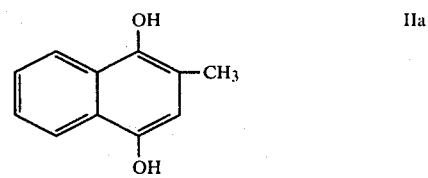

which comprises heating the compound IIIa or the compound IIIb

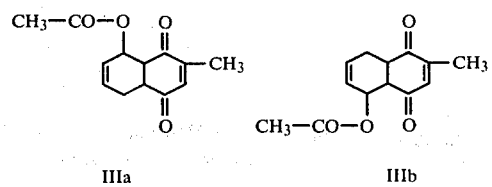

or a mixture thereof at a temperature of no more than 200° C. and/or treating said compounds IIIa or IIIb or a mixture thereof with a non-oxidizing acid.

5. A process for preparing vitamin $K_4$ diacetate having the structure

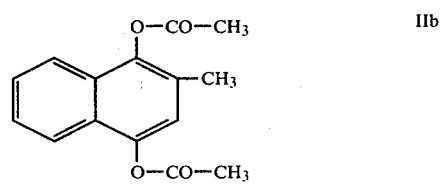

which process comprises heating the compound IIIa or the compound IIIb or a mixture thereof together with acetic anhydride to a temperature of from 50° to 150° C., and thereafter isolating the compound IIb.

6. A process for preparing vitamin $K_3$, said compound having a formula

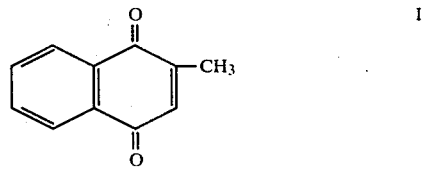

which process comprises heating the compound IIIa or the compound IIIb or a mixture thereof together with an oxidizing agent to a temperature of 20° to 100° C.

* * * * *